United States Patent [19]

Washer et al.

[11] Patent Number: 4,467,131
[45] Date of Patent: Aug. 21, 1984

[54] HF ALKYLATION PROCESS AND APPARATUS

[75] Inventors: Stone P. Washer; Joe Van Pool, both of Bartlesville, Okla.

[73] Assignee: Phillips Petroleum Company, Bartlesville, Okla.

[21] Appl. No.: 493,841

[22] Filed: May 12, 1983

[51] Int. Cl.³ .............................................. C07C 2/58
[52] U.S. Cl. ..................................................... 585/723
[58] Field of Search ........................................ 585/723

[56] References Cited

U.S. PATENT DOCUMENTS

| | | | |
|---|---|---|---|
| 3,006,739 | 10/1961 | Van Pool | 585/723 |
| 3,239,578 | 3/1966 | Samuelson | 585/719 |
| 3,729,526 | 4/1973 | Anderson | 585/706 |
| 4,053,535 | 10/1977 | Hutson | 585/720 |

Primary Examiner—Curtis R. Davis
Attorney, Agent, or Firm—Bernhard H. Geissler

[57] ABSTRACT

In an HF alkylation process the HF phase leaving the reaction zone is introduced into a separate resaturation zone wherein this HF phase is contacted with isobutane to resaturate the HF with isobutane. In the main hydrocarbon fractionator only a very small quantity of isobutane has to be evaporated and this isobutane can be withdrawn as a side stream and recycled.

11 Claims, 1 Drawing Figure

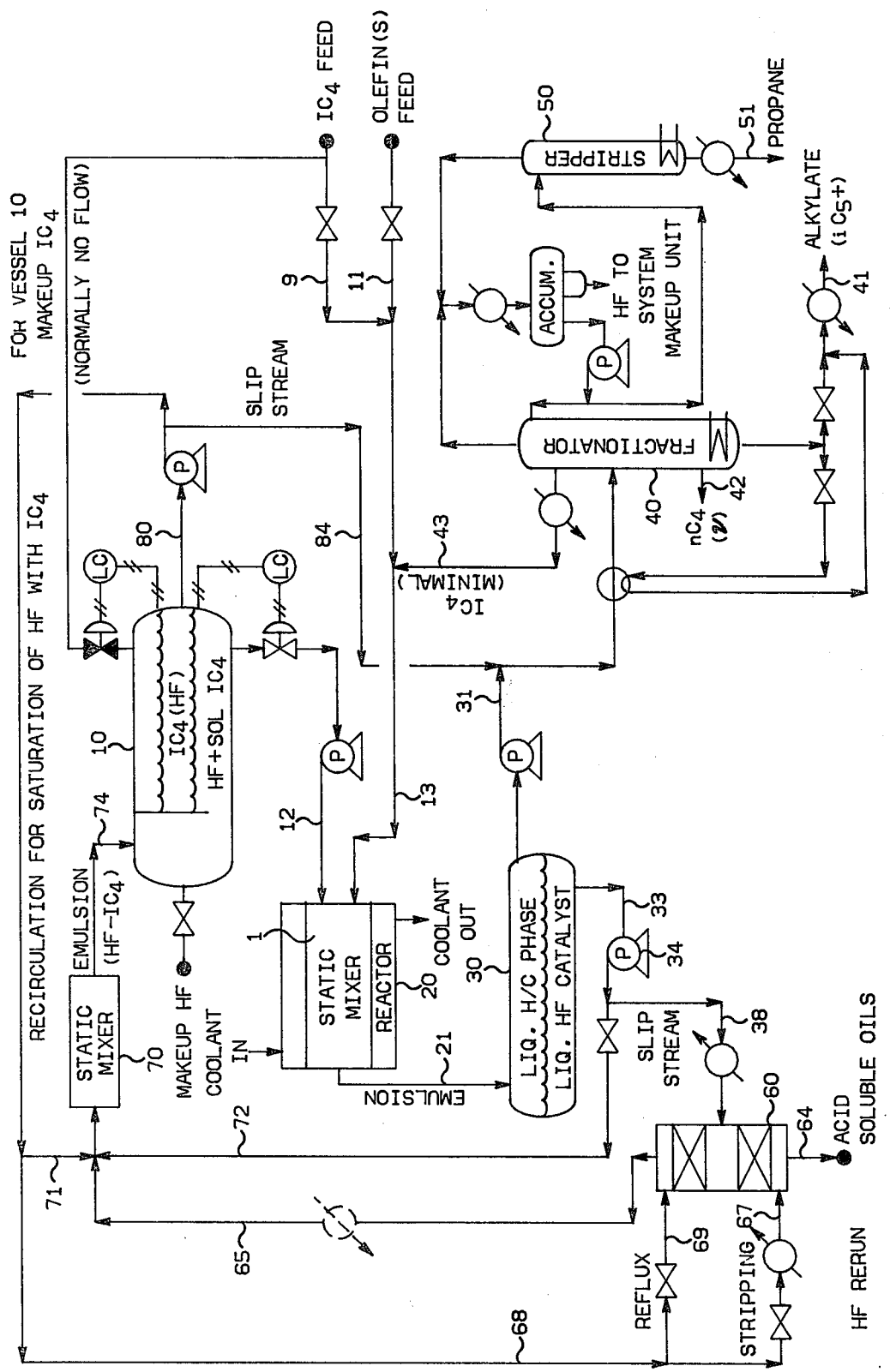

HF ALKYLATION PROCESS AND APPARATUS

The present invention relates to a modified HF alkylation process. In another aspect the invention relates to a reduction in size of the hydrocarbon fractionator in an HF alkylation process and system.

BACKGROUND OF THE INVENTION

HF alkylation is a developed and mature technology. In an HF alkylation process olefins, isoparaffins and HF are intimately contacted with each other such as to produce an alkylate. Phase separation and recycling of HF as well as fractionation of the organic phase are known steps in the art.

Generally, the exothermic HF alkylation reaction is carried out with a substantial excess of isoparaffins over the olefins. U.S. Pat. No. 3,006,739 discloses an isobutane to olefin volume ratio of 14.1:1. This large excess of isobutane or other isoparaffin in an HF alkylation process requires a separation of the excess isoparaffin from the alkylate. Usually this is achieved by evaporating the isoparaffin. Such an evaporation of a large volume of isobutane requires not only a significant amount of energy but necessitates fairly large hydrocarbon fractionators.

The Invention

It is thus one object of this invention to provide an HF alkylation process using less energy for hydrocarbon separation.

Another object of this invention is to provide an HF alkylation system which is both energy efficient and does not require commercially prohibitive captial investments.

These and other objects, details, features, embodiments and advantages of this invention will become apparent to those skilled in the art from the following detailed description of the invention, the appended claims and the drawing which shows a schematic flow diagram for the system and process of this invention.

In accordance with this invention an HF alkylation system is provided for wherein in an indirect heat exchanger a hydrocarbon mixture and HF are contacted to form alkylate. The invention uses as one of the feed materials to the reaction an HF which has been saturated with isobutane and employs only a minor amount (if any) of isobutane in the hydrocarbon feed material entering the reaction zone. Preferably the ratio of free isobutane to isobutane dissolved in HF is less than about 1.4/1, and most preferably is in the range of about 0.5/1 to about 1.2/1. The isobutane to olefin ratio is preferably low, namely in the range of about 2:1 to 4:1 by volume. In this process the HF catalyst leaving the indirect heat exchanger is removed from the reaction product and resaturated with isobutane. In the preferred embodiment of this invention the isobutane to olefin ratio is increased by (1) increased HF circulation, (2) increased HF temperature in the resaturation step and (3) decreasing the olefin feed.

One of the major differences in this invention and previous alkylation is that the major amount of isobutane is supplied in the HF acid. Since previous alkylation supplied isobutane in large quantities to assure transfer to the HF phase for reaction the present system will produce equivalent reaction with a lower overall isobutane to olefin ratio in the alkylation zone. This also results in a greatly reduced fractionator load since much of the required isobutane is supplied by solution in HF.

Thus in a first embodiment of this invention a process for producing alkylate is provided. In an indirect heat exchanger an HF stream essentially saturated with isobutane and a feed material of isobutane and olefin are contracted to produce a mixture of two liquid phases. Preferably, the volume ratio of HF to total hydrocarbon in the indirect heat exchanger is in the range of about 2:1 to about 10:1. Furthermore, the volume ratio of total isobutane to olefin in the indirect heat exchanger is preferably in the range of about 2:1 to 5:1. Increasing the isobutane to olefin ratio produces benefits (increased quality and quantity) at the expense of circulating more isobutane saturated HF. The upper limit of isobutane to olefin ratio will be determined by economics. The term "total isobutane" refers to the sum of the feed isobutane and the isobutane dissolved in the saturated HF stream. At least a substantial portion of the HF phase which is not saturated with isobutane is then resaturated in a resaturation zone usually by mixing the HF with isobutane. Thereby an HF phase saturated with isobutane is produced and this HF phase saturated with isobutane is introduced into the alkylation reaction. It is important to note that the saturation of the HF with isobutane is carried out in the absence of olefin.

The resaturation step is preferably carried out by mixing the HF with isobutane in a mixer such as a static mixer. The effluent emulsion from this mixer is then introduced into a settler. Since it is preferred to operate in this resaturation mixing step with an excess of isobutane, the effluent emulsion from the mixer contains a significant amount of isobutane. This emulsion is then phase separated in a settler and the HF phase now again saturated with isobutane is removed as the lower liquid phase from this settler. This lower liquid phase is introduced as the HF stream into the indirect heat exchanger. The upper hydrocarbon phase comprising the excess isobutane is removed from the settler and this isobutane stream is preferably recycled to the mixer wherein the HF phase is resaturated with isobutane.

The emulsion effluent from the indirect heat exchanger containing HF, isoparaffin, n-paraffin and a small amount of alkylate is phase separated into an HF phase and a hydrocarbon phase. The HF phase, as pointed out, is not saturated with isobutane. The hydrocarbon phase contains only a small amount of isobutane. This hydrocarbon phase is subjected to fractionation, and an alkylate stream is recovered from the bottom of the hydrocarbon fractionator. Preferably a small side draw stream rich in isobutane is also withdrawn from the fractionator. In the process of this invention the total quantity of isobutane in the hydrocarbon fractionator is very small as compared to the conventional alkylation process. Therefore, the fractionator as a whole can be smaller and the small volume of isobutane only has to be evaporated in such a fractionator. The side draw of isobutane is recycled either to the indirect heat exchanger in which the HF alkylation reaction takes place or to the resaturation mixture in which the HF phase is resaturated with isobutane.

Since hydrocarbons other than isobutane are somewhat soluble in the HF catalyst it is presently preferred to withdraw a slip stream of isobutane from the phase separator of the resaturation unit and to introduce this slip stream into the main hydrocarbon fractionator. Thereby hydrocarbons other than isobutane are withdrawn from the resaturation loop and thus from the HF. The alkylate is recovered through the bottom of the hydrocarbon fractionator.

It is also preferred in accordance with this invention to subject a slip stream of the HF phase from the main reaction to a removal of acid soluble oils, or to a stripping step. Such a step can be carried in a rerun tower, and preferably is done by utilizing an isobutane vapor stream for stripping and liquid isobutane for reflux. The thus purified HF is then resaturated with isobutane if necessary. This is preferably done in the same resaturation zone as the one where the main HF phase is resaturated with isoparaffin.

HF Alkylation Process

Except for the isobutane to olefin ratio and the HF to total hydrocarbon ratio the operating conditions and potential starting materials for the HF alkylation process of this invention are the same as for known processes. Thus, olefins having 3 to 6 carbons atoms can preferably be utilized. The process is particularly well applicable to an alkylation process using isobutane and butenes. Typical operating conditions for the HF alkylation reaction include a temperature range of about 70° to 110° F., a pressure of 100 to 180 psi and a contact time of approximately 10 to 60 seconds. The resaturation of the HF phase with isobutane is carried out under conditions which can be closely the same as those of the alkylation reaction. It is, however, in the scope of this invention to utilize resaturation conditions which are more conducive to the resaturation of HF with isobutane. Thus, it is particularly preferred to carry out the resaturation of the HF phase at a temperature about 10° to 20° F. higher than the temperature of the HF alkylation reaction.

In the drawing an HF stream saturated with isobutane is introduced into an indirectly cooled reactor which is preferably a indirectly cooled static mixer 1 by way of line 12. Olefin feedstock from line 11 and isobutane feedstock from line 9 are introduced together via line 13 into the indirectly cooled reactor 1. In this reactor 1 an emulsion is formed and the exothermic alkylation reaction takes place. The emulsion effluent is withdrawn from reactor 1 via line 21 and introduced into a phase separator 30. From this phase separator 30 a liquid hydrocarbon phase is withdrawn via line 31 and introduced into a main fractionator 40. The liquid HF phase withdrawn from the phase separator 30 via line 33 is pumped by means of pump 34 through line 72 into a static mixer 70. In this static mixer 70 the HF phase, which in line 33 is not saturated with isobutane, is resaturated with isobutane from line 71 and/or from line 65.

A small slip stream of the HF catalyst is introduced via line 38 into rerun tower 60. In this tower 60 the slip stream of HF is stripped using vaporized recirculated isobutane from line 68 and using liquid reflux via line 69. The gaseous HF/isobutane effluent in line 65 is substantially free of acid soluble oils which leave the rerun tower 60 via line 64.

The emulsion effluent from the static mixer 70 is introduced via line 74 into a phase separating settler 10. From the phase separator 10 isobutane, containing some HF, is withdrawn via line 80. This isobutane stream is used for resaturation of the HF phase via line 71 and/or in the rerun tower via line 68. A lower liquid phase which is HF saturated with isobutane is withdrawn from the settler 10 and introduced into the static mixer 1 via line 12.

A small slip stream of isobutane from line 80 is introduced via line 84 into the hydrocarbon fractionator 40. Thereby n-butane, isopentane, n-pentane and small amounts of alkylate are removed from the isobutane stream.

From the fractionator 40 a small stream of isobutanes is withdrawn via line 43 as a liquid stream. This stream is preferably added to the hydrocarbon feedstock, line 13, for alkylation reaction in the static mixer reactor 1. The drawing also shows the typical condensation, accumulation and stripping in stripper 50 of the main fractionator overhead which comprises, for example, propane. This propane is withdrawn from the stripper via line 51. Normal butane is withdrawn from the fractionator 40 via line 42 while alkylate is recovered via line 41.

The following constitutes a calculated example of operating conditions and stream compositions for a typical isobutane/butene alkylation system incorporating the present invention. The individual stream numbers refer to the drawing.

Calculated Example

| Calculated Example | |
|---|---|
| I. Operating Conditions: | |
| (10) Phase Separator: | |
| Pressure, psig., | 75 |
| Temperature, °F. | 90 |
| (20) Static-Mixer Reactor (including conduit to 30): | |
| Pressure, psig., | 90 |
| Temperature, °F., | 80 |
| IC₄/Olefin vol. ratio | 2.3 |
| (Inlet) HF base/Total HC vol. ratio | 2.7 |
| Residence Time, sec., | 30 |
| (30) Phase Separator: | |
| Pressure, psig., | 74 |
| Temperature, °F., | 80 |
| (40) Fractionator: | |
| Pressure, psig., | 260 |
| Temperature, °F., | |
| Top, | 125 |
| Bottom, | 350 |
| (50) Stripper: | |
| Pressure, psig., | 270 |
| Temperature, °F., | |
| Top, | 125 |
| Bottom, | 133 |
| (60) HF Rerun: | |
| Pressure, psig., | 100 |
| Temperature, °F., | |
| Top, | 260 |
| Bottom, | 340 |
| (70) Static Mixer: | |
| Pressure, psig., | 90 |
| Temperature, °F., | 90 |
| II. Flow Amounts and Compositions: | |
| (9) Isobutane Feed, B/H, (95% iC₄ by volume) | 25.9 |
| (11) Olefin Feed, B/H, | 192.2 |
| Component | Vol. % |
| Isobutylene, | 15 |
| n-Butenes | 37 |
| iC₄, (nC₄, C₃) | 48 |
| Total | 100 |
| (12) HF-Isobutane, B/H, | 1070.4 |
| Component | Vol % |
| HF(+ ASO + H₂O) | 89.85 |
| iC₄ | 9.65 |
| Other H/C | 0.50 |
| Total | 100.00 |
| (21) Reactor Effluent, B/H, | 1280.8 |

-continued

| Calculated Example | |
|---|---|
| (31) Hydrocarbon Phase, B/H, | 210.6 |
| Propane, B/H, | 1.0 |
| Normal Butane, B/H, | 11.2 |
| Isobutane, B/H, | 24.6 |
| IC$_5$ plus (alkylate), B/H, | 173.8 |
| (41) Alkylate, B/H, | 184.2 |
| (42) Normal Butane, B/H, | — |
| (51) Propane, B/H, | 0.5 |
| (43) iC$_4$, B/H, | 25.9 |
| (71) Recycle IC$_4$, B/H, | 503 |
| (72) Recycle HF, B/H, | 1070.2 |
| (has iC$_4$ and other H/C) | |

Reasonable variations and modifications which will become apparent to those skilled in the art can be made in this invention without departing from the spirit and scope thereof.

What is claimed is:

1. Process for producing alkylate comprising
   (a) contacting in an indirect heat exchanger an HF stream essentially saturated with isobutane and a feed material of isobutane and olefin to produce a mixture of at least two liquid phases, comprising an HF phase and a hydrocarbon phase,
   (b) phase separating said mixture into said HF phase and said hydrocarbon phase containing said alkylate,
   (c) resaturating at least a substantial portion of said HF phase with isobutane in a separate resaturation zone, comprising a mixer followed by a settler, wherein said HF phase is introduced together with excess isobutane into said mixer to form a resaturation emulsion, wherein said resaturation emulsion is introduced from said mixer into said settler, wherein said liquid HF phase saturated with isobutane is removed as the lower liquid phase from said settler and wherein an isobutane stream is removed as an upper liquid phase from said settler and this isobutane stream is recycled to said mixer, and
   (d) introducing at least a portion of the so obtained liquid HF phase saturated with isobutane to said contacting step (a) as said HF stream.

2. Process in accordance with claim 1 comprising introducing said hydrocarbon phase into a fractionator to recover a bottom stream comprising mainly alkylate and a small side stream comprising isobutane.

3. Process in accordance with claim 1 comprising introducing a portion of said upper liquid phase as a slip stream as well as said hydrocarbon phase into a fractionator such as to recover alkylate in a bottom stream and to withdraw a small side stream of isobutane from said fractionator.

4. Process in accordance with claim 3 comprising reintroducing said small side stream of isobutane as a portion of said feed material into said indirect heat exchanger and/or as a portion of said isobutane into said resaturation zone.

5. Process in accordance with claim 1 comprising introducing as a slip stream a portion of said HF phase to an acid rerun tower for removal of acid soluble oils and water as necessary to maintain the desired system acid strength and returning the overhead stream from said acid rerun tower comprising HF and isobutane to said resaturation zone.

6. Process in accordance with claim 1 wherein said indirect heat exchanger is an indirectly cooled static mixer.

7. Process in accordance with claim 1 wherein said olefin comprises predominantly butene.

8. Process in accordance with claim 1 wherein in said indirect heat exchanger the ratio of free isobutane to isobutane dissolved in HF is less than about 1.4/1.

9. Process in accordance with claim 1 wherein said indirect heat exchanger the ratio of isobutane to olefin is in the range of about 2:1 to about 4:1 by volume.

10. Process in accordance with claim 1 wherein the volume ratio of HF to total hydrocarbon in said indirect heat exchanger is in the range of about 2:1 to about 10:1.

11. Process in accordance with claim 1 wherein in said indirect heat exchanger
    (a) the ratio of free isobutane to HF dissolved isobutane is in the range of about 0.5/1 to about 1.2/1, and
    (b) the volume ratio of isobutane to olefin is in the range of about 2:1 to about 4:1, and
    (c) the volume ratio of HF to total hydrocarbon is in the range of about 2:1 to about 10:1.

* * * * *